United States Patent
Gu et al.

(10) Patent No.: US 6,995,001 B2
(45) Date of Patent: Feb. 7, 2006

(54) PROCESSING FOR PREPARING MONOPROTECTED DIOLS FROM SYMMETRIC DIOLS

(75) Inventors: Jianxin Gu, New Milford, NJ (US); Mark Edward Ruppen, Garnerville, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 245 days.

(21) Appl. No.: 10/672,788

(22) Filed: Sep. 26, 2003

(65) Prior Publication Data

US 2004/0067564 A1    Apr. 8, 2004

Related U.S. Application Data

(60) Provisional application No. 60/415,880, filed on Oct. 3, 2002.

(51) Int. Cl.
*C12P 7/62* (2006.01)
(52) U.S. Cl. ..................................... 435/135
(58) Field of Classification Search ................. 435/135
See application file for complete search history.

(56) References Cited

FOREIGN PATENT DOCUMENTS

WO    WO 97/22710    6/1997

OTHER PUBLICATIONS

Manfred T. Reetz, 2002, Lipases as practical biocatalysts, Current Opinion in Chem. Biology, 6, 145-150.
Per Berglund and Karl Hult, Biocatalytic Synthesis of Enantiopure Compounds Using Lipases, Royal Institute of Technology, Stockholm, Sweden, 21, 633-653 . . . .
Houille et al, 1996, A remarkably Simple Process for Monoprotecting Diols,. Tetrahedron Letters, 37;5.
Allevip, et al: Lipase-catalysed chemoselective monoacetylation of hydroxyalkylphenols and chemoselective removal of a single acetyl group from their diacetates, Tetrahedron: Asymmetry 9:2915-2924 (1998).
Ciuffreda P. et al: Lipase-catalyzed monoprotection of 1,4-diols in an organic solvent using vinyl benzoate as acyl transfer agent, Tetrahedron Letters 44:3663-3665 (2003).
Banfi L, et al: On the Optimization of Pig Pancreatic Lipase Catalyzed Monoacetylation of Prochiral Diols, Tetrahedron: Asymmetry 6:6:1345-1356 (1995).
Levayer F, et al: Enzyme catalysed resolution of 1,3-diarylpropan-1,3-diols, Tetrahedron: Asymmetry 6:7:1675-1682 (1995).

*Primary Examiner*—Herbert J. Lilling
(74) *Attorney, Agent, or Firm*—Joy S. Goudie

(57) ABSTRACT

This invention provides a two-step enzymatic process for the synthesis of monoprotected diols from symmetric diols.

20 Claims, No Drawings

PROCESSING FOR PREPARING MONOPROTECTED DIOLS FROM SYMMETRIC DIOLS

"This application claims priority from copending provisional application, application Ser. No. 60/415,880 filed Oct. 3, 2002, the entire disclosure of which is hereby incorporated by reference".

BACKGROUND TO THE INVENTION

This invention provides a two-step enzymatic process for the synthesis of monoprotected diols from symmetric diols.

Selective protection of diols having the general formula HO—$(CH_2)_n$—OH remains a challenge. Frequently, treatment of these diols with a stoechiometric amount of a reagent aimed at forming a derivative of the hydroxy functionality results in the formation of a 1/2/1 mixture of unreacted diol, the monoprotected and the bis-protected derivative respectively. Houille, Olivier et al., *A Remarkably Simple Process for Monoprotecting Diols*, Tetrahedron Letters, Vol. 37, No. 5, 1996, pp. 625–628.

Chemical synthesis of a monoprotected diol from a symmetric diol employing routing acetylation procedures has proven to be unfeasible due to poor selectivity and low yield with poor reproducibility. The procedure presented in the O. Houille paper (Id.) proved to be unpractical due to the lack of commercial availability of starting material and use of lipase (PPL) produced from animal sources. Our procedure of this invention employs two commercially available lipases from microorganisms.

This convenient process can be utilized to synthesize other monoprotected diols from symmetric diols.

BRIEF SUMMARY OF THE INVENTION

This invention provides a process for producing a compound of the formula:

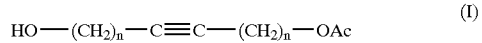
(I)

wherein n=1–5 which comprises (a) mixing a compound of the formula:

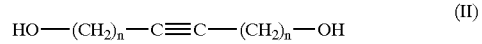
(II)

with an effective amount of a first lipase, an acyl donor, and an optional organic solvent to yield a crude mixture of monoacetate and diacetate of the formulas:

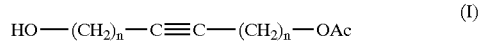
(I)

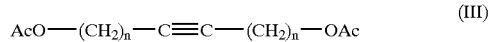
(III)

(b) suspending the crude mixture in a buffer with a second lipase to yield an extractable monoacetate and diacetate of formulas (I) and (III); and (c) purifying the extracted monoacetate to a compound of formula (I) having a purity of at least 98% and a yeild of at least 50%.

In one embodiment of the invention the temperature maintained in the reaction of the first lipase, the acyl donor, and the optional organic solvent is about 20° C. to about 70° C. In a prefered embodiment the temperature is about 30° C. to about 55° C. In the most prefered embodiment the temperature is about 40° C.

After teatment of diol with two lipases, HPLC showed the ratio of diol:monoacetate:diacetate=2.5:90:7.5 with a yield of monoacetate 80%. This is a much improved result over conventional chemical method which theoretically give a maximum yield of 50% at the ratio of 25:50:25 (diol:monoacetate:diacetate) as being mentioned in O. Houille paper. Since our procedure only use enzymes as clean substitutes for standard organic chemical reagents, the overall operation is simple, and has proven to be easy to scale-up with reproducible yield. Further purification gives monoacetate in good yield with high purity.

In one embodiment of the invention the time for completion of the reaction of the first lipase, the acyl donor, and the optional organic solvent to yield the crude mixture of monoacetate and diacetate is about 3 hours to about 15 hours. In a prefered embodiment the time is about 5 hours to about 10 hours. In the most prefered embodiment the time is about 8 hours.

In an embodiment of the invention the organic solvent is optional to the reaction. For example the acyl donor is also the organic solvent with no additional organic solvent added to the reaction mixture. Type of organic solvent used is dependent on the acyl donor used in the reaction. A sufficient amount of organic solvent is used which effectively dissolves the reactants and allows the reaction to proceed at a reasonable rate to the formation of the crude mixture of monoacetate and diacetate. Organic solvents that may be used in the reaction include, but are not limited to, tetrahydrofuran, ethyl acetate, acetonitrile, toluene, hexane, ethyl ether, tert-butylmethyl ether (TBME).

For purposes of this invention the acyl donor is a compound that reacts with a lipase to give an acyl-enzyme intermediate, an acyl acceptor, which is usually water but can be any nucleophile such as alcohols. For example, a compound of formula (II) in this invention reacts with an acyl enzyme to form the crude mixture of formula (I) and (III). Nonlimiting examples of acyl donors are isopropenyl acetate and vinyl acetate. See, Per Berflund and Karl Hult, *Biocatalytic Synthesis of Enantiopure Compounds Using Lipases*, In Ramesh N. Patel, eds. *Sterioselective Biocatalysis*, Marcel Dekker, 2000, pages 633–653, hereby incorporated by reference.

For purposes of this invention the first lipase and second lipase are hydrolytic enzymes capable of acting on an acyl donor or an acyl acceptor. An effective amount of both lipases is the amount of lipase used to allow the reaction to proceed at a reasonable rate to the formation of the crude mixture. The first lipase is capable of acylating the compound of formula (I) in organic solvent in the absence of water to form a mixture of monoacetate and diacetate. Examples of lipases include, but are not limited to AMANO A (supplier—Amano, source—*Aspergillus niger*), AMANO LIPASE AY (Boehringer Mannheim—*Candida cylindracea*), Novozym SP-435 (Novo—*Candida antarctica*), AMANO LIPASE GC (Sigma, Amano—*Geotrichum candidum*), AMANO MAP-10 LIPOZYME (Amano, NOVO, Fluka—*Mucor miehei*), AMANO P, PS. (Amano, Fluka—*Pseudomonas cepacia*), AMANO AK, K-10 (Amano—Pseudomonas sp.).

In one embodiment of the invention the temperature maintained in the reaction of the second lipase and the crude mixture is about 20° C. to about 55° C. In the most prefered embodiment the temperature is about 24° C.

In one embodiment of the invention the time for completion of the reaction of the second lipase and the crude mixture of monoacetate and diacetate is about 4 hours to about 12 hours. In a prefered embodiment the time is about 5 hours to about 10 hours. In the most prefered embodiment the time is about 8 hours.

In one embodiment of the invention the pH of the reaction of the second lipase and the crude mixture of monoacetate and diacetate is about 5.0 to about 8.5. In a prefered embodiment the pH is about 6.8 to about 6.85.

The buffer of this invention can be any standard aqueous buffer solution. The selection of the buffer and the concentration of the buffer would be such to maintain the crude mixture and second lipase at or near a pH of from about 5.0 to about 8.5. Examples of buffers include but are not limited to 0.05 M potassium hydrogen phthalate, 0.25 M potassium dihydrogen phosphate, 0.05 M disodium hydrogen phosphate, and 0.1 M borax. In a prefered embodiment the buffer is a 0.1 M phosphate buffer.

For purposes of this invention an example of the compound of formula (I) is 4-hydroxy-2-butynyl acetate.

The following experimental details are set forth to aid in an understanding of the invention, and are not intended, and should not be construed, to limit in any way the invention set forth in the claims that follow thereafter.

DETAILED DESCRIPTION OF THE INVENTION

A two-step enzymatic process was developed for the synthesis of a monoprotected diol using lipase NOVOZYME SP435 and AMANO PS. First, a symmetric diol was acylated in organic solvent using vinyl acetate or isopropenyl acetate as acyl donor catalyzed by NOVOZYME SP435, the resulted mixture of corresponding mono and diacetate was then subjected to another lipase (AMANO PS) catalyzed hydrolysis to yield the desired product.

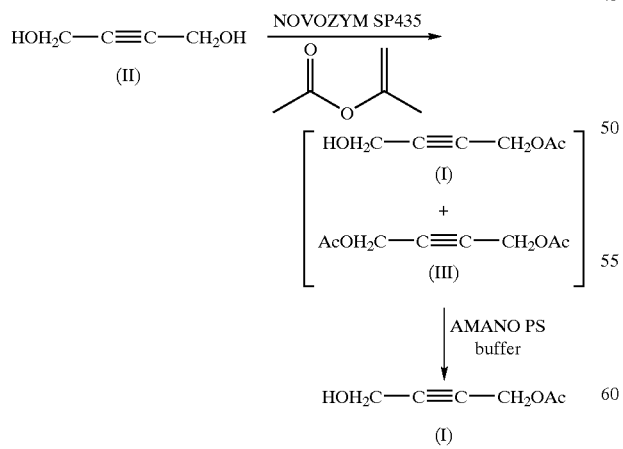

(a) A mixture of 2-butyne-1,4-diol (II) (86g, 1 mol) and NOVOZYME SP435 (3 g) in isopropenyl acetate or vinyl acetate (860 mL) was stirred at 40° C. for 8h (either monitored by TLC or HPLC). The enzyme was removed via filtration. Concentration under reduced pressure gave a crude mixture of diacetate (III) and monoacetate (I) (diol:monoacetate:diacetate=1.5:28:66) which was used without further purification.

(b) Above crude mixture was suspended in 0.1 M phosphate buffer (1100mL, pH 7.2)[2] and AMANO PS (4 g) was added. The mixture was stirred at room temperature (24° C.) while the pH was maintained at 6.8–6.85 by adding 5N NaOH[3] (about 140 mL) during a period of 8 h[4]. The mixture was extracted with EtOAc (2×1500 mL). The combined organic layers were concentrated under reduced pressure to give the crude product as a light yellow oil (about 114 g). HPLC showed the ratio of diol:monoacetate:diacetate=2.5:90:7.5, yield of monoacetate 80%.

(c) Purification of the above product is done by suspending the crude in $H_2O$ (750 mL). The mixture was washed with hexane/EtOAc (750 mL, 9:1 v/v)[5]. After the separation of organic layers, the aqueous layers were extracted with EtOAc/hexane (2×750 mL, 4:1 v/v). The combined organic layers were dried ($MgSO_4$), filtration and concentration under reduced pressure gave monoacetate (I) as a light yellow oil (85 g)[6]. HPLC showed the ratio of diol:monoacetate:diacetate=0.4:94.7:4.4.

(d) Futher purification can be performed by silica gel chromatography. 360 grams silica gel (230–400 mesh) was packed at 75 mm (I.D.)/20 cm (height) and 50 g of sample (from procedure B) was loaded, then eluted with solvent EtOAc/Hexane (1:1), the fractions containing monoacetate were collected, HPLC showed >98% purity.

Note:
1. HPLC conditions: C18 column (150×4.4 mm), gradient elution with eluent A and eluent B (1–10 minutes, 100% A, 10–25 minutes, 100% A to 100% B, 26–30 minutes 100% B to 100% A). Eluent A ($H_2O$:MeCN:$CF_3COOH$=90:10:0.01), eluent B ($H_2O$:MeCN:$CF_3COOH$=50:50:0.01).
2. The final pH dropped to 6.8 when crude mixture was added to pH 7.2 phosphate buffer.
3. The theoretical amount of NaOH can be calculated based on the ration of monoacetate and diacetate in the crude.
4. A model 718 titrino titrator from Brinkmann Metrohm was used.
5. About 4 g of the mixture of diacetate and monoacetate (3:1) was obtained.
6. A third time extraction of aqueous layer with EtOAc can recover about 16–18 g of product as a mixture of diol and monoacetate (5:95) which can be recycled.

What is claimed is:
1. A process for producing a compound of the formula:

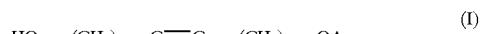

wherein n=1–5
which comprises
(a) mixing a compound of the formula:

with an effective amount of a first lipase which acts on anacyl donor, an acyl donor, and an optional organic solvent to yield a crude mixture of monoacetate and diacetate of the formulas:

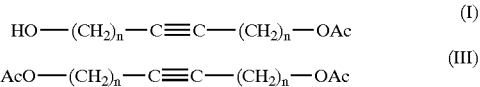

(b) suspending the crude mixture in a buffer with a second lipase which acts on the acyl acceptor to yield an extractable monoacetate and diacetate of formulas (I) and (III); and (c) purifying the extracted monoacetate to a compound of formula (I) having a purity of at least 98% and a yeild of at least 50%.

2. The process of claim 1 wherein the temperature in step (a) is about 20° C. to about 70° C.

3. The process of claim 1 wherein the temperature in step (a) is about 30° C. to about 55° C.

4. The process of claim 1 wherein the temperature in step (a) is about 40° C.

5. The process of claim 1 wherein the time in step (a) is about 3 hours to about 15 hours.

6. The process of claim 1 wherein the time in step (a) is about 5 hours to about 10 hours.

7. The process of claim 1 wherein the time in step (a) is about 8 hours.

8. The process of claim 1 wherein the organic solvent comprises tetrahydrofuran, ethyl acetate, acetonitrile, toluene, hexane, ethyl ether, tert-butylmethyl ether (TBME).

9. The process of claim 1 wherein the acyl donor is isopropenyl acetate.

10. The process of claim 1 wherein the acyl donor is vinyl acetate.

11. The process of claim 1 wherein the first lipase is a hydrolytic enzyme acting on an acyl donor.

12. The process of claim 1 wherein the second lipase is a hydrolytic enzyme acting on an acyl acceptor.

13. The process of claim 1 wherein the temperature of step (b) is about 20° C. to about 55° C.

14. The process of claim 1 wherein the temperature of step (b) is about 24° C.

15. The process of claim 1 wherein the time of step (b) about 4 hours to about 12 hours.

16. The process of claim 1 wherein the time is about 5 hours to about 10 hours.

17. The process of claim 1 wherein the time is about 8 hours.

18. The process of claim 1 wherein the pH is about 5.0 to about 8.5.

19. The process of claim 1 wherein the pH is about 6.8 to about 6.85.

20. The process of claim 1 wherein the compound of formula (I) is 4-hydroxy2-butynyl acetate.

* * * * *